US009618332B2

(12) United States Patent
Zhang (10) Patent No.: US 9,618,332 B2
(45) Date of Patent: Apr. 11, 2017

(54) METHOD AND APPARATUS FOR POSITION DETERMINATION (75) Inventor: Fucai Zhang, Didcot (GB)

(73) Assignee: PHASE FOCUS LIMITED, Sheffield, South Yorkshire (GB)

(*) Notice: Subject to any disclaimer, the term of this patent is extended or adjusted under 35 U.S.C. 154(b) by 760 days.

(21) Appl. No.: 14/232,524

(22) PCT Filed: Jul. 13, 2012

(86) PCT No.: PCT/GB2012/051681
§ 371 (c)(1),
(2), (4) Date: Apr. 4, 2014

(87) PCT Pub. No.: WO2013/008034
PCT Pub. Date: Jan. 17, 2013

(65) Prior Publication Data
US 2014/0207409 A1    Jul. 24, 2014

(30) Foreign Application Priority Data
Jul. 14, 2011 (GB) .................................. 1112119.1

(51) Int. Cl.
*G01B 11/14* (2006.01)
*G01N 23/04* (2006.01)

(52) U.S. Cl.
CPC .......... *G01B 11/14* (2013.01); *G01N 23/046* (2013.01); *G01N 2223/419* (2013.01)

(58) Field of Classification Search
CPC .................................................. G01B 11/14
See application file for complete search history.

(56) References Cited

U.S. PATENT DOCUMENTS

| 5,552,605 A | 9/1996 | Arata |
| 2005/0010108 A1* | 1/2005 | Rahn ................ G01N 15/1468 600/425 |

(Continued)

FOREIGN PATENT DOCUMENTS

| WO | 03/012822 | 2/2003 |
| WO | 2006/011945 | 2/2006 |

(Continued)

OTHER PUBLICATIONS

Hurst, A. C. et al., "Probe position recovery for ptychographical imaging," Journal of Physics: Conference Series, vol. 241, (2010), 012004, pp. 1-4.

(Continued)

*Primary Examiner* — Manual Rivera Vargas
(74) *Attorney, Agent, or Firm* — MH2 Technology Law Group, LLP (57) ABSTRACT Embodiments of the invention provide a method of determining a position of an object with respect to incident radiation, comprising iteratively determining at least one of an object function indicating one or more characteristics of an object and a probe function indicative of one or more characteristics of incident radiation, iteratively determining the position of the object, wherein the iteratively determining the position of the object comprises cross correlating first and second estimates of the object function or the probe function, determining a location of a peak of the cross correlation, and determining a translation deviation indicative of a difference in position of the object between the first and second estimates based on the location of the peak.

33 Claims, 7 Drawing Sheets

(56) References Cited

U.S. PATENT DOCUMENTS

2007/0071357 A1    3/2007  Rahn et al.
2011/0235863 A1*   9/2011  Maiden .................... G01T 1/00
                                                      382/103

FOREIGN PATENT DOCUMENTS

WO    2010/064051    6/2010
WO    2012/073043    6/2012

OTHER PUBLICATIONS

Maiden, Andrew M. et al., "An improved ptychographical phase retrieval algorithm for diffractive imaging," Ultramicroscopy, vol. 109, (2009), pp. 1256-1262.
Martin, A.V. et al., "A method for correcting the effect of specimen drift on coherent diffractive imaging," Ultramicroscopy, vol. 110, Iss. 4, (Mar. 2010), pp. 359-365.
Hue, F. et al., "Extended ptychography in the transmission electron microscope: Possibilities and limitations," Ultramicroscopy, vol. 111, Iss. 8, (Jul. 2011), pp. 1117-1123.
Takahashi, Yukio et al., "Towards high-resolution ptychographic x-ray diffraction microscopy," Physical Review B, vol. 83, (2011), pp. 214109-1-214109-4.
Search Report and Examination Opinion dated Jul. 6, 2012 from Great Britain Application No. 1112119.1 filed Jul. 14, 2011, pp. 1-7.
International Search Report and Written Opinion dated Oct. 16, 2012 for PCT Int'l Application No. PCT/GB2012/051681 filed Jul. 13, 2012, pp. 1-8.
International Preliminary Report on Patentability dated Jan. 23, 2014 from International Application No. PCT/GB2012/051681, pp. 1-5.

* cited by examiner

METHOD AND APPARATUS FOR POSITION DETERMINATION

CROSS-REFERNECE TO RELATED APPLICATIONS

This application is a U.S. National Stage application of International Application No. PCT/GB2012/051681 filed Jul. 13, 2012, which claims priority to Great Britain Application No. 1112119.1 filed Jul. 14, 2011, the entire disclosure of which are hereby incorporated by reference in their entireties.

BACKGROUND

The present invention relates to methods and apparatus for determining a position of an object in relation to incident radiation. In particular, although not exclusively, some embodiments of the invention may be used to improve a quality of data relating to the object or the radiation.

WO 2005/106531, which is incorporated herein by reference for all purposes, discloses a method and apparatus of providing image data for constructing an image of a region of a target object. Incident radiation is provided from a radiation source at the target object. An intensity of radiation scattered by the target object is detected using at least one detector. The image data is provided responsive to the detected radiation. A method for providing such image data via an iterative process using a moveable probe function is disclosed. The methods and techniques disclosed in WO 2005/106531 are referred to as a ptychographical iterative engine (PIE).

PIE provides for the recovery of image data relating to at least an area of a target object from a set of diffraction pattern measurements or to the determination of information associated with radiation illuminating the target object. Several diffraction patterns are recorded at a measurement plane using one or more detectors, such as a CCD or the like.

WO 2010/064051, which is incorporated herein by reference for all purposes, discloses an enhanced PIE (ePIE) method wherein it is not necessary to know or estimate a probe function. Instead a process is disclosed in which the probe function is iteratively calculated step by step with a running estimate of the probe function being utilised to determine running estimates of an object function associated with a target object.

Other methods are known which are referred to a coherent diffraction imaging (CDI) which are based on the measurement of scattered radiation, such as that by P Thibault, Dierolf, et al entitled "Probe Retrieval in Ptychographic Coherent Diffractive Imaging" disclosed in Ultramicroscopy, 109, 1256-1262 (2009) and WO2011033287 entitled "Method And Apparatus For Retrieving A Phase Of A Wavefield", which is herein incorporated by reference, by the present inventor.

In some of the above methods, particularly the ptychography methods, movement between a plurality positions is often required i.e. to record a plurality of diffraction patterns with the illumination located differently with respect to the object. In some methods, the movement is relative movement between the object and the radiation or probe. To achieve such movement, the object, probe or both may be moved or translated amongst a plurality of positions. The probe may be moved by altering a position of the radiation source, focussing optics or an aperture. The object may be moved upon, for example a translation stage. The accuracy of such movements presents a limitation on the accuracy of the resultant image data.

In other methods, particularly the coherent diffraction imaging methods, only a single diffraction pattern is required to be recorded. However, it is difficult to eliminate drift of the illuminating radiation and/or the object to within the accuracy required by such methods.

Embodiments of the invention aim to improve a determination of a position based on recorded intensity measurements.

It is an object of embodiments of the invention to at least mitigate one or more of the problems of the prior art.

SUMMARY OF THE INVENTION

According to a first aspect of the present invention there is provided a method of determining a position of an object with respect to incident radiation, comprising cross correlating first and second estimates of an object function indicating one or more characteristics of the object or a probe function indicative of one or characteristics of the incident radiation, and determining a peak of the cross correlation, wherein the location of the object with respect to the incident radiation is based at least in part on a location of the peak.

The method may include estimating a wave front at a plane of a detector based on the object function and the probe function. A portion of the wave front may be updated based on the detected radiation. The updating of the wave front or the portion of the wave front may comprise updating a modulus of the wave front according to the detected radiation.

Optionally, the method may comprise detecting an intensity of radiation scattered by the target object with the incident radiation or the post target aperture at a first position with respect to the target object. The incident radiation or the post-target aperture may be repositioned at least one further position relative to the target object. The repositioning may be caused by movement of a translation means, such as a stage, or may be caused by drift of the radiation source, aperture or the object. Subsequently, the method may comprise detecting the intensity of radiation scattered by the target object with the incident radiation or post-target aperture at the at least one further position.

Optionally, the method may comprise estimating the object function indicating at least one characteristic of said region of the target object; and/or estimating the probe function indicating at least one characteristic of incident radiation; and iteratively re-estimating each of the object function and/or probe function.

Optionally, the method may comprise multiplying the estimated object function by the estimated probe function to thereby provide an exit wave estimate; propagating the exit wave function to provide an estimate of an expected scattering pattern or wave front at the detector; and correcting at least one characteristic of said expected scattering pattern according to a detected intensity of radiation scattered by the target object.

Optionally, the method may comprise inversely propagating a corrected expected scattering pattern to thereby provide an updated exit wave function.

A propagation operator BP may suitably model the propagation between the plane of the object and the measurement plane. BP may comprise a Fourier Transform or a Fresnel Transform.

Optionally, the method may comprise updating a running estimate of the probe function and/or a running estimate of an object function simultaneously with at least some iterations of the method.

Optionally, the method may further comprise providing an initial estimate of the probe or object function as a prior modelled probe or object function. The initial estimate of the probe or object function may be provided by a random approximation for the probe function.

Optionally, wherein the target object may be at least partially transparent to the incident radiation and detecting an intensity of radiation scattered by the target object may comprise detecting an intensity of radiation transmitted by the target object.

Optionally, the target object may be at least partially reflective to the incident radiation and detecting an intensity of radiation scattered by the target object may comprise detecting an intensity of radiation reflected by the target object.

According to a second aspect of the present invention there is provided an apparatus for determining a position of an object with respect to incident radiation, comprising a detector for measuring an intensity of a wavefield incident thereon scattered from an object, and a processing device arranged to receive intensity data from the detector and to determine the position of the object with respect to the incident radiation by cross correlating first and second estimates of an object function indicating one or more characteristics of the object or a probe function indicative of one or characteristics of the incident radiation and determining a peak of the cross correlation, wherein the location of the object with respect to the incident radiation is based at least in part on a location of the peak.

The apparatus may be arranged for providing image data for constructing an image of a region of a target object, comprising a data store storing data indicating an intensity of radiation scattered by a target object with the incident radiation or an aperture at a predetermined probe position, wherein the processing means is arranged to determine the location of the object, estimate a wavefront based on the probe function and the object function, and to provide image data responsive to the detected radiation.

The processing means may be arranged to provide the image data via an iterative process responsive to the detected radiation with incident radiation or an aperture at first and second positions.

The processing means may be arranged to estimate at least one of the object function indicating at least one characteristic of at least a region of the target object and/or the probe function indicating at least one characteristic of incident radiation at the target object or the aperture. The processing means may further be arranged to estimate a wave front at a plane of the at least one detector based on the object function and the probe function. The processing means may be further arranged to update the wave front based on the detected radiation.

The processing means may be arranged to update a modulus of wave front or the portion of the wave front according to the detected radiation.

Embodiments of the invention are useful to determine the location of the object with respect to the incident radiation. The location of the object may be determined substantially in real time i.e. on-the-fly determination of the location of the object with respect to the incident radiation. Some embodiments of the invention may be used provide image data having an improved resolution. Some embodiments of the invention improve a rate of convergence a method of determining the image data. Some embodiments of the invention reduce a noise present in the image data.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Figure 1:
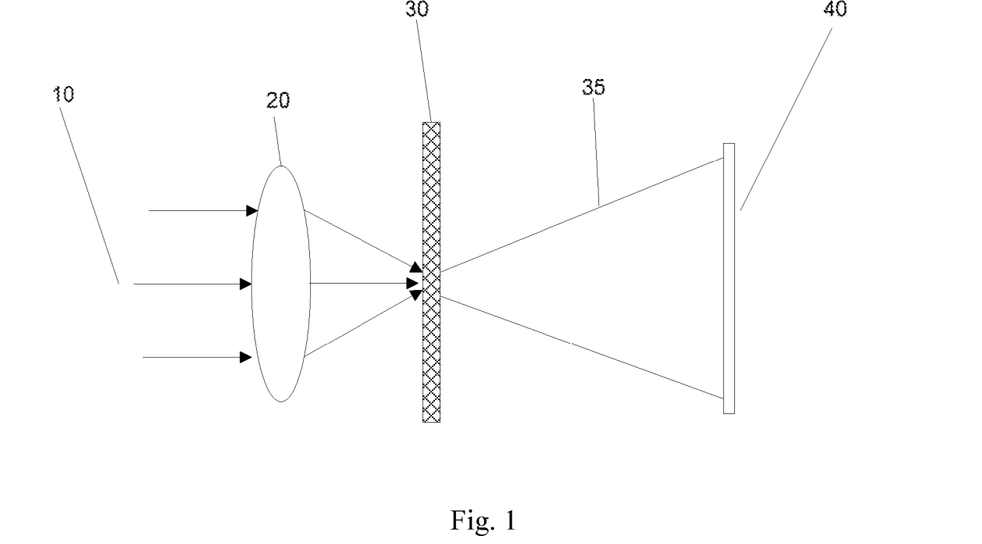
FIG. 1 shows an apparatus according to an embodiment of the invention.

FIG. 1 illustrates an apparatus 100 according to an embodiment of the invention. The apparatus is suitable to provide image data of an object which may, although not exclusively, be used to produce an image of at least a region of the object. The apparatus 100 may also be used to determine one or more attributes of radiation illuminating the object. The apparatus 100 may also be used to determine the relative displacement between the incident radiation and the object.

A radiation source, which although not shown in FIG. 1, is a source of radiation 10 which falls upon a focusing arrangement 20, such as one or more lenses, and is caused to illuminate a region of a target object 30. It is to be understood that the term radiation is to be broadly construed. The term radiation includes various wave fields. Radiation includes energy from a radiation source. This will include electromagnetic radiation including X-rays, emitted particles such as electrons. Other types of radiation include acoustic radiation, such as sound waves. Such radiation may be represented by a wave function $\psi(r)$. This wave function includes a real part and an imaginary part as will be understood by those skilled in the art. This may be represented by the wave functions modulus and phase.

The lens 20 forms a probe function $P(r)$ which is arranged to select a region of the target object 20 for investigation. The probe function selects part of an object exit wave for analysis. $P(r)$ is the complex stationary value of this wave field calculated at the plane of the object 40.

It will be understood that rather than weakly (or indeed strongly) focusing illumination on the target 40, unfocused radiation can be used with a post target aperture. An aperture is located post target object to thereby select a region of the target for investigation. The aperture is formed in a mask so that the aperture defines a "support". A support is an area of a function where that function is not zero. In other words outside the support the function is zero. Outside the support the mask blocks the transmittance of radiation. The term aperture describes a localised transmission function of radiation. This may be represented by a complex variable in two dimensions having a modulus value between 0 and 1. An example is a mask having a physical aperture region of varying transmittance.

Incident radiation thus falls upon the up-stream side of the target object 30 and is scattered by the target object 30 as it is transmitted. The target object 30 should be at least partially transparent to incident radiation. The target object 30 may or may not have some repetitive structure. Alternatively the target object 30 may be wholly or partially reflective in which case a scattering pattern is measured based on reflected radiation.

An exit wave $\psi(r)$ is formed after interaction of the illuminating radiation with the object 30. In this way $\psi(r)$ represents a two-dimensional complex function so that each point in $\psi(r)$, where r is a two-dimensional coordinate, has associated with it a complex number. $\psi(r)$ will physically represent a wave that would emanate from the object 30. For example, in the case of electron scattering, $\psi(r)$ would represent the phase and amplitude alteration as a result of passing through the object 30 of interest which is illuminated by a plane wave. The probe function P(r) selects a part of the object exit wave function for analysis. It will be understood that rather than selecting an aperture, a transmission grating or other such filtering function may be located downstream of the object. The probe function P(r) is an aperture transmission function. The probe function can be represented as a complex function with its complex value given by a modulus and phase which represent the modulus and phase alterations introduced by the probe into a perfect plane wave incident up it.

This exit wave $\psi(r)$ may form a diffraction pattern $\Psi(k)$ at a diffraction plane. Here k is a two-dimensional coordinate in a detector plane.

It will be understood that if the diffraction plane at which scattered radiation is detected is moved nearer to the specimen then Fresnel diffraction patterns will be detected rather than Fourier diffraction patterns. In such a case the propagation function from the exit wave $\psi(r)$) to the diffraction pattern $\Psi(k)$ will be a Fresnel transform rather than a Fourier transform. It will also be understood that the propagation function from the exit wave $\psi(r)$) to the diffraction pattern $\Psi(k)$ may be modelled using other transforms.

In order to select the region of the target object 30 to be illuminated or probed, the lens(es) 20 or aperture may be mounted upon an x/y translation stage which enables movement of the probe function with respect to the object 30. Equally, it will also be realised that the object 30 may be moved with respect to the lens(es) 20 or aperture.

The relative translation can be implemented by moving a translation stage in a grid arrangement of positions or a spiral arrangement among any others. It is also possible to rely on drift of probe or object to provide the translation diversities i.e. without using a translation stage or other means to cause movement of, for example, the object.

A detector 40 is a suitable recording device such as a CCD camera or the like which allows the diffraction pattern to be recorded. The detector 40 allows the detection of the diffraction pattern in a detector plane i.e. a plane different from that of the object. The detector 40 may comprise an array of detector elements, such as in a CCD.

In some methods such as those disclosed above, the object and/or radiation source, lens 20 or aperture are moved amongst a plurality of positions (translations). In some embodiments, some of the positions cause the illuminated object region to at least partially overlap that of other illuminated object regions. A diffraction pattern is recorded at each translation position. It has been noted that the accuracy with which the translation position can be determined may limit the accuracy of the image data, which consequently limits a resolution of an image produced using the image data. This problem may be particularly acute with radiation having a relatively short wavelength, such as X-ray and electron radiation, although the present invention is not limited to use with these types of radiation. With such radiation, a target resolution may be <50 nm and accurate determination of the translation position to such accuracy is difficult.

Figure 2:
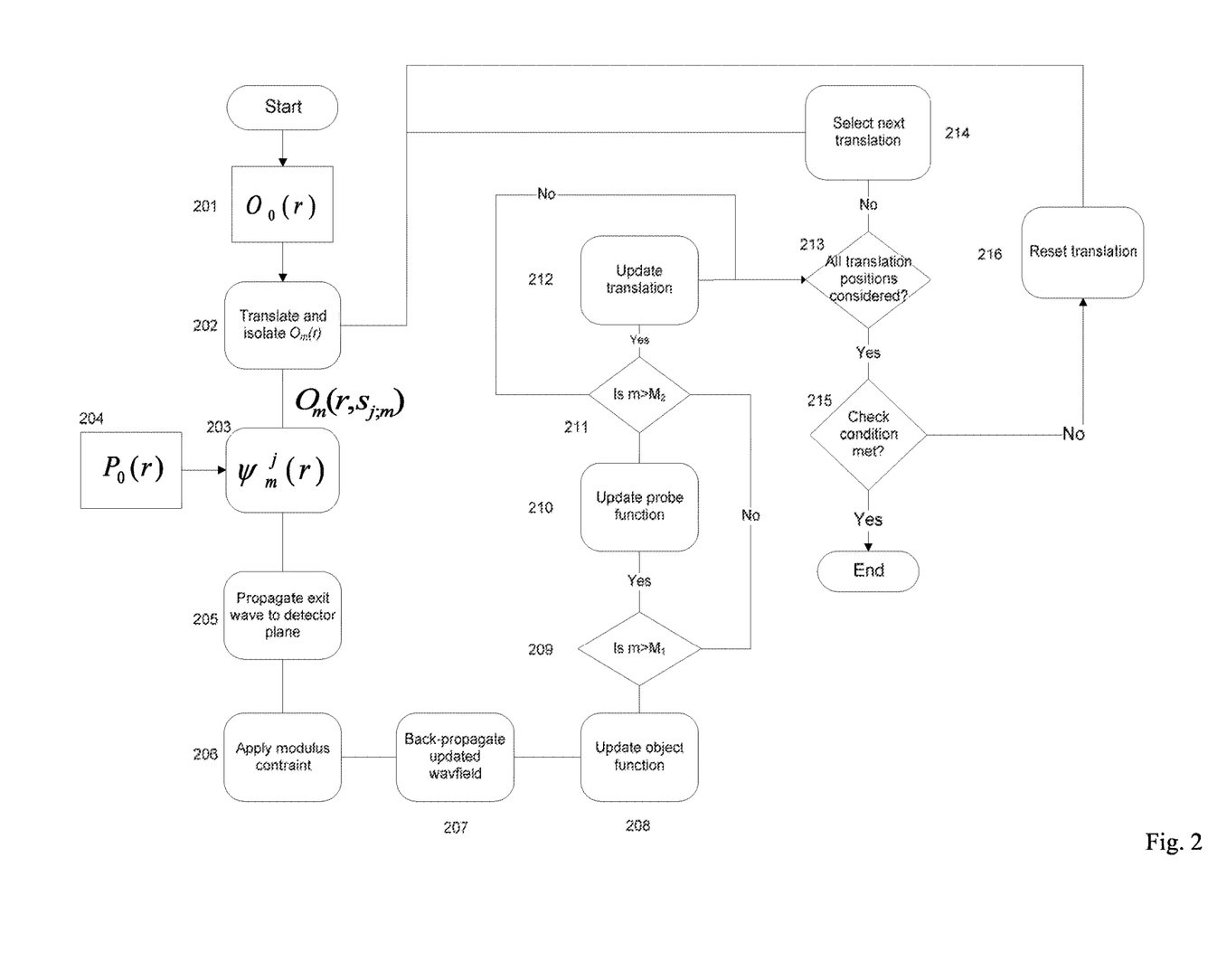
FIG. 2 shows a method according to an embodiment of the invention.

FIG. 2 illustrates a method 200 according to an embodiment of the invention. The method determines one or more positions of an object with respect to incident radiation based on recorded intensity measurements, as will be explained.

The method 200 illustrated in FIG. 2 involves, for at least some iterations, simultaneous, step-by-step updating of both probe and object function estimates. However, it will also be realised that embodiments of the invention may be envisaged in which only the object function is updated and a known probe function is used, as in the methods and apparatus disclosed by WO 2005/106531 or vice versa as in Physics Review A 75 043805 (2007), for example. It will also be appreciated that the object function and/or probe function may be updated by other methods, such as that by Thibault et al. In some iterations of the method, an estimate of a translation position is updated, as will be explained.

The method 200 utilises a set of J intensity measurements or diffraction patterns, $I_j(k)$, recorded by the detector 40, where k is a position vector at the detector plane. Each of the J diffraction patterns may be associated with a different translation position of the object or probe.

During some iterations of the method, estimates of the probe function, object function, and/or translation shift are updated for each of the J diffraction patterns measured by the detector 40. In some embodiments, during an initial first plurality of iterations of the method 200, the probe function P(r) is not updated, only the object function O(r) is updated. However, it will be realised that embodiments of the invention may be envisaged in which the probe function P(r) is updated during every iteration of the method 200, or where the probe function P(r) is not updated at all, as noted above. Still further, it will be realised that embodiments of the invention may be envisaged where only the probe function P(r) is updated, or where the object function O(r) is only updated after the initial first plurality of iterations. After an initial second plurality of iterations of the method a translation shift estimate $s_j$ is updated, as will be explained. The second plurality may be the same as the first plurality of iterations, or the translation shift estimate $s_j$ may be updated for every iteration of the method 200.

In embodiments of the invention, a translation difference $e_j$ is determined during at least some iterations of the method. However, it will be realised embodiments of the invention may be envisaged wherein the translation difference $e_j$ is determined during every iteration of the method.

An order of considering each of the J measured intensities is chosen. The order may be numerically sequential i.e. j=1, 2, 3 . . . J. In this case, beginning with diffraction pattern 1 and progressing through to J, updated estimates of the object $O(r,s_1) \ldots O(r,s_j)$ and, for some iterations, also the probe P(r) and the translation shift $s_1, s_2, \ldots s_j$ are produced. However, considering the diffraction patterns in a raster fashion (each pattern in a row sequentially and each row sequentially) may cause problems particularly in relation to the estimate of the probe function drifting during the method. Therefore, in some embodiments, the diffraction patterns may be considered in another pseudo-random order. However, for the purposes of explanation, a sequential ordering of 1, 2, . . . J will be considered.

For each diffraction pattern, a portion of the object is recorded. In the described embodiments, movement of the object function is described as being achieved by movement of the object 30. However, it will be realised that the lens 20 or an aperture may alternatively be moved to change the location of the probe with respect to the object 30.

In step 201 an initial guess for an object function $O_0(r)$ is provided. The subscript 0 indicates that this is an estimate of the object function for a $0^{th}$ iteration of the method 200 i.e. an initial guess for the object function $O(r)$. The initial guess may be a matrix where all positions are 1 or may have values selected according to one or more approximations of the object function representing the initial guess of the object function.

In step 202 an object function corresponding to a location of the object 30 for the $j^{th}$ diffraction pattern is determined. The object function may be determined by shifting the entire object function estimate $O_m(r)$ by $s_{j,m}$, the $j^{th}$ object translation shift, and extracting the central region which is the same size as the probe function estimate $P_m(r)$ and denoted as $O_m(r, s_{j,m})$ where m denotes the current iteration number.

Figure 3:
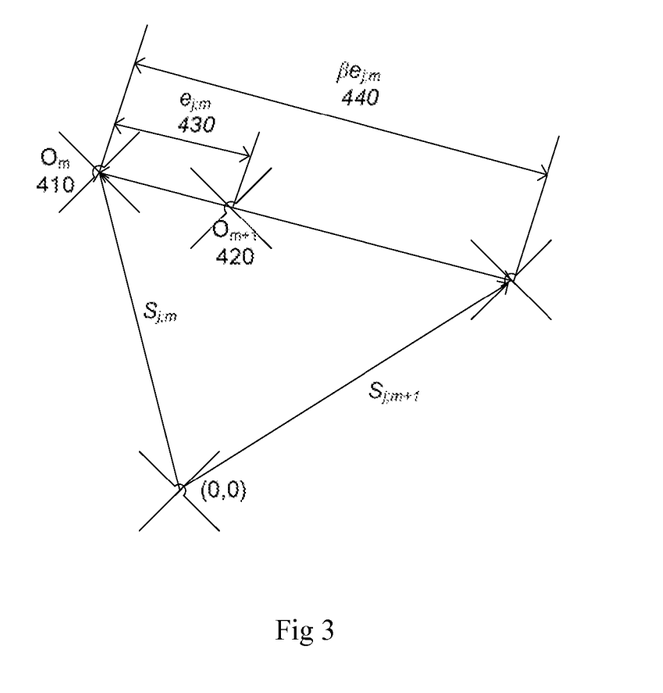
FIG. 3 illustrates a series of correction vectors determined according to an embodiment of the invention.

FIG. 3 illustrates the translation shift position vector. The translation shift vector $s_j$ indicates a location of the object function with respect to a reference which, in this example, is an origin point (0,0), although other reference points may be used.

In step 203, an exit wave $\psi_m^j(r)$ from the object 30 is determined for the $j^{th}$ object translation. The exit wave is determined by multiplying the current estimates of the object function for that position $O_m(r, s_{j,m})$ and the probe function $P_m(r)$ which, for a first (m=0) iteration of step 203, is an initial guess of the probe function $P_0(r)$ 204, as in Equation 1:

$$\psi_m^j(r) = P_m(r)O_m(r, s_{j,m}) \qquad \text{Equation 1}$$

In step 205 the exit wave $\psi_m^j(r)$ is propagated to a plane of the detector 40. The propagation may be achieved by applying a beam propagation operator BP to the exit wave. For far field diffraction, BP is a Fourier transform. However, embodiments of the invention may be envisaged in which BP is another transform, such as a Fresnel function, particularly where the detector 40 is located in the near field from the specimen 30. The propagation of the exit wave to the plane of the detector 40 produces an estimate of the object wavefield at the plane of the detector 40 $\Psi_m^j(k)$, as in Equation 2:

$$\Psi_m^j(k) = BP<\psi_m^j(r)> \qquad \text{Equation 2}$$

In step 206 a modulus constraint is applied to the estimate of the wavefield at the plane of the detector. In some embodiments, the modulus of the estimated diffracted field is replaced with a square root of an intensity $\sqrt{I_j(k)}$ measured by the detector 40.

$$\tilde{\Psi}_m^j(k) = \frac{\Psi_m^j(k)}{|\Psi_m^j(k)|}\sqrt{I_j(k)} \qquad \text{Equation 3}$$

where the symbol ~ is used to indicate an updated estimate.

In step 207 the updated estimate of the object wavefield determined in step 206 is back-propagated to the object plane. The back-propagation is performed using an inverse of the beam propagator used in step 205, as in Equation 2, to determine an updated estimate of the exit wave at the object plane $\tilde{\psi}_m^j(r)$ as follows:

$$\tilde{\psi}_m^j(r) = BP^{-1}<\tilde{\Psi}_m^j(k)> \qquad \text{Equation 4}$$

In step 208 an updated estimate of the object function $O_{m+1}(r, s_j)$ is determined. The object function is updated by applying an overlap constraint. The overlap constraint specifies that the object function retrieved from each diffraction pattern must be consistent in their overlapped regions. The overlap constraint may be defined as in Equation 5:

$$O_{m+1}(r, s_j) = O_m(r, s_j) + U(r)[\tilde{\psi}_m^j(r) - \psi_m^j(r)] \qquad \text{Equation 5}$$

Where U(r) is a weighting update function which may be related to the probe function. The form of the weighting update function may be chosen appropriate for the method employed. However, a particular form for the weighting update function is provided by Equation 6:

$$U(r) = \frac{\alpha_1 P_m^*(r)}{|P_m(r)|_{max}^2} \qquad \text{Equation 6}$$

which leads to robust but rapid convergence where $\alpha_1$ assumes a value of between 0 and 2, although other limits for $\alpha_1$ may be chosen.

In step 209, in some embodiments of the invention, it is determined whether the number of the current iteration is greater than a predetermined number $M_1$. If the current iteration number m is greater than $M_1$, then the method moves to step 210 where the probe function is updated.

The probe function is updated in step 210 by applying the overlap constraint, similar to the transmission function, in step 208, by Equation 7:

$$P_{m+1}(r) = P_m(r) + \alpha_2 \frac{O_m^*(r, s_j)}{|O_m(r, s_j)|_{max}^2}[\tilde{\Psi}_m^j(r) - \Psi_m^j(r)] \qquad \text{Equation 7}$$

where $\alpha_2$ assumes a value of between 0 and 2, although other limits for $\alpha_2$ may be chosen.

It will be appreciated from the above that each portion of the object function $O(r)$ is updated during each iteration of the method 200 to provide an image of the object. In the presence of position errors in the translation shift $s_j$, the operation of stitching or combining object function portions $O_m(r, s_j)$ for the plurality of translation positions to form the overall object function estimate $O_m(r)$ results in errors in $O_m(r)$.

However, it has been observed that the retrieved transmission function estimate at each translation position $O_m(r, s_j)$ gradually moves toward its correct position as a consequence of the modulus and overlap constraints. In embodiments of the invention, a relative shift between an updated transmission function estimate $O_{m+1}(r, s_j)$ and the previous estimate of the transmission function $O_m(r, s_j)$ are utilised to correct an error present in the translation shift $s_j$.

In step 211, in some embodiments of the invention, it is determined whether the number of the current iteration m is greater than a predetermined number $M_2$. If the current iteration number m is greater than $M_2$, then the method moves to step 212. If not, the method moves directly to step 213.

In step 212 the translation for the current object position $s_{j,m}$ is updated. In embodiments of the invention, the translation shift is updated based upon a relative shift between the object function updated in step 208 and the former object function i.e. $O_{m+1}(r,s_j)$ and $O_m(r,s_j)$, respectively. The translation shift may be updated according to Equation 8:

$$s_{j;m+1} = s_{j;m} + \beta \cdot e_{j;m} \qquad \text{Equation 8}$$

where $e_{j;m}$ is a translation deviation between the successive object function estimate for the $j^{th}$ translation position.

The parameter $\beta$ controls a strength of feedback of the translation deviation to the translation shift. The parameter $\beta$ may be static i.e. fixed for all iterations of the method, or may be dynamically adjusted in response to one or more criteria, as will be explained. The value of $\beta$ may be selected according to a level of structure of the probe and/or object functions. Structure rich probe and/or object functions are suited to a relatively lower value of $\beta$, whereas weakly structures probe and/or object functions are suited to a larger value of $\beta$. The value of $\beta$ influences a speed of convergence of embodiments of the invention. If $\beta$ is chosen to be too large for the structure of the probe and/or object functions, then $e_{j;m}$ may fluctuate rather than converging. A value of $\beta=1$ should always lead to convergence, although values of $\beta=1$ to several tens may be useful.

In some embodiments of the invention, the translation deviation $e_{j;m}$ is determined based on cross-correlation between the object function $O_m(r,s_{j,m})$ and the updated object function $O_{m+1}(r,s_{j,m})$ i.e. cross-correlation between successive estimates of the object function. It will be realised that it would also possible to cross-correlate between non-adjacent estimates of the object function i.e. between $O_x(r,s_j)$ and $O_y(r,s_j)$ where $x>y+1$. In particular, embodiments of the invention are arranged to determine a peak of a cross correlation function between the object function $O_m(r,s_j)$ and the updated object function $O_{m+1}(r,s_j)$. The translation deviation $e_{j;m}$ 430 is shown in FIG. 3 in relation to successive estimate of the object function 410, 420. It can be appreciated from FIG. 3 that the extent to which the translation shift $s_j$ is updated depends upon the value of $\beta$.

The peak of the cross correlation function may be determined according to Equation 9:

$$R(t) = \sum_r O_{m+1}(r, s_{j;m}) O_m^*(r-t, s_{j;m}) = \qquad \text{Equation 9}$$

$$\sum_f \hat{O}_{m+1}(f, s_j) \hat{O}_m^*(f, s_j) \exp\left(2i\pi f \cdot \frac{t}{N}\right)$$

where $\hat{O}_m(f,s_j)$ and $\hat{O}_{m+1}(f,s_j)$ are the Fourier transform of $O_m(r,s_j)$ and $O_{m+1}(r,s_j)$, where f is spatial frequency; N is the linear size of array $\hat{O}_m(r,s_j)$. The peak location of which is denoted as $t_{max}$ i.e.

$$R(t_{max}) = \max_t \{R(t)\}.$$

The cross correlation function may be evaluated in either the space or frequency domain. However, it may be preferable to compute the cross correlation function in the frequency domain to reduce an execution time or computational resources of determining the cross correlation function.

Figure 4:
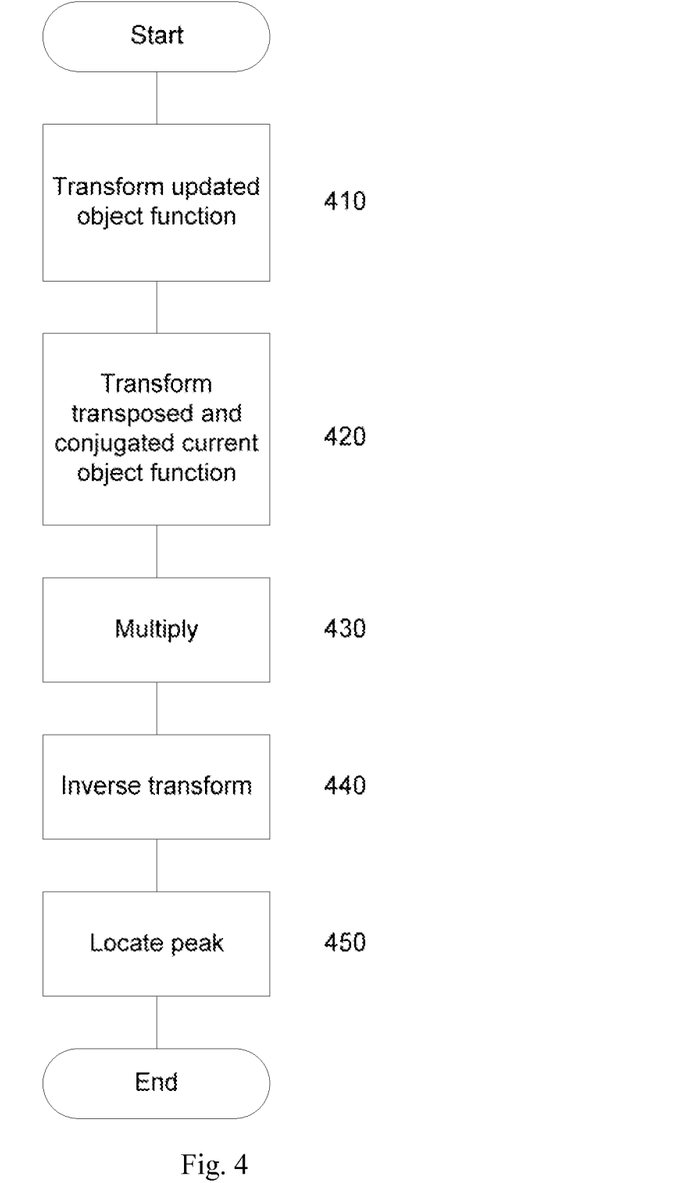
FIG. 4 shows a further method according to an embodiment of the invention.

Assuming that the transmission function is stored as a 2D array where $O_m(r,s_j)$ and $O_{m+1}(r,s_j)$ are N×N arrays, an integer part of the shift deviation $e_{j;m}$ may be determined using the method shown in FIG. 4.

In step 410 a Fourier transform of the updated object function $O_{m+1}(r,s_j)$ is determined. The Fourier transform of the object function may be determined by means of a discrete Fourier transform (DFT) as in Equation 10:

$$\hat{O}_{m+1}(f,s_j) = DFT_{N \times N} <O_{m+1}(r,s_j)> \qquad \text{Equation 10}$$

In step 420 a DFT of a transposed and conjugated current estimate of the object function $O^*_m(-r,s_j)$ is determined. The DFT of the transposed and conjugated current estimate of the object function may be determined as in Equation 11:

$$\hat{O}^*_m(f,s_j) = DFT_{N \times N} <O^*_m(-r,s_j)> \qquad \text{Equation 11}$$

In step 430 the results of steps 410 and 420 are multiplied as in Equation 12:

$$\hat{R}(f) = \hat{O}_{m+1}(f,s_j) \hat{O}^*_m(f,s_j) \qquad \text{Equation 12}$$

In step 440 the result of step 430 is inversely transformed to yield R(t).

In step 450 a peak position of an amplitude of the cross correlation function R(t) is determined, which may be denoted as (ix, iy). This forms an integer part of $e_{j;m}$.

In some embodiments of the invention, a sub pixel deviation of the translation is determined. The sub-pixel deviation may be determined by performing the inverse Fourier transform in step 340 at a finer grid in real space. In some embodiments, this is achieved by zero-padding $\hat{R}(f)$. In some embodiments, such as where R(t) has only a single peak, only a small region around the peak is needed to be evaluated to determine the sub-pixel shift, in which case direct matrix multiplication may be computationally more efficient than zero padding $\hat{R}(f)$.

Returning to FIG. 2, in step 213 it is determined whether all translation positions have been considered. In other words, whether each of the J measured intensities has been considered. If not, the method moves to step 214 where a next measured intensity is chosen. The next measured intensity may be selected by incrementing j or by another means, such as pseudo-random selection of the next value of j. If all translation positions have been considered then, in step 215, it is determined whether a check condition has been met. The check condition may be a predetermined number of iterations, or may be a check on an error metric associated with one or more of the object function, probe function or translation shifts. If the check condition is met the method ends. Otherwise, the method moves to step 216 where a reset occurs i.e. to—repeat an another iteration using the updated estimates of the probe and object functions, as well as the translation positions As an example, FIG. 5 illustrates the position determined of embodiments of the invention used to update translation shifts for a plurality of object positions.

Figure 5:
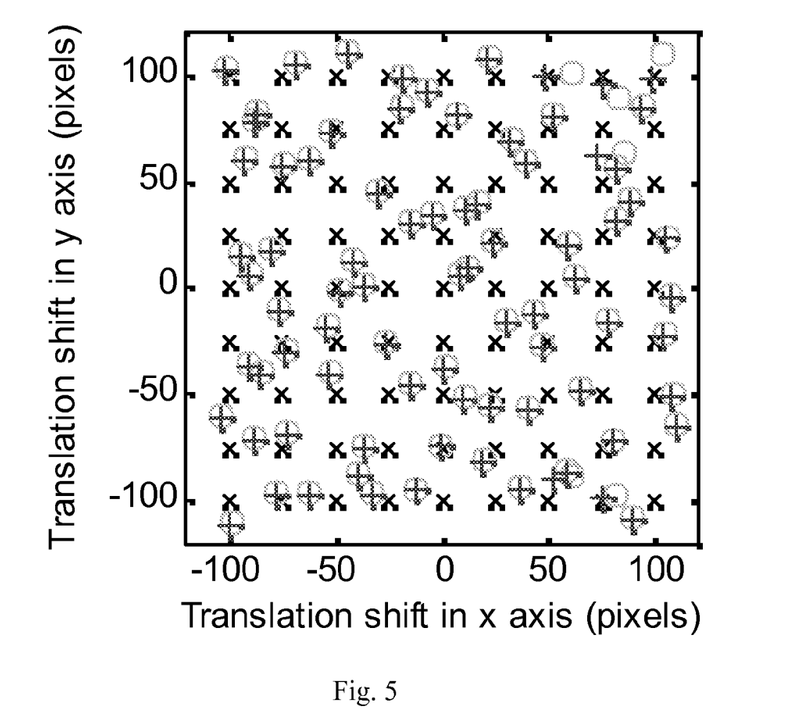
FIG. 5 shows an illustration of position data determined according to an embodiment of the invention.

Diagonal crosses in FIG. 5 indicate original translation shift positions i.e. m=0. Following 100 iterations of a method according to an embodiment of the invention, the crosses formed by vertical and horizontal lines indicate updated translation shift positions in comparison to correct translation shift positions which are indicated by circles. It can be appreciated that a large amount of error existed between the originally estimated translation shift positions and the correct positions, whereas the updated translation shift positions are much more accurate i.e. closer to the correct positions indicated by circles.

Whilst the use of an initial estimate for the translation shift positions provides quicker convergence to the actual translation shift positions, embodiments of the invention may be used where the initial translation shift positions are unknown i.e. each translation shift position is set to (0,0), for example. Thus it is not necessary to know or to have an initial translation shift position estimate.

Figure 6A:
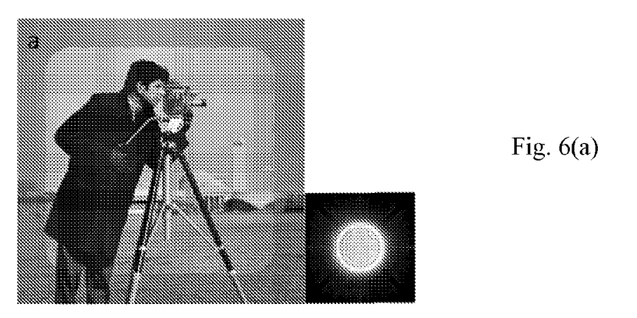
FIG. 6 shows images of an example object and probe.
Figure 6B:
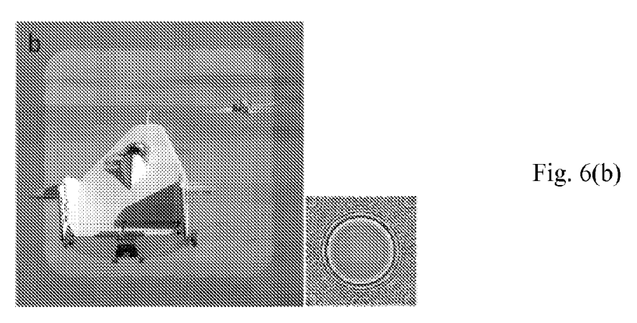

FIG. 6 indicates example object and probe functions. FIG. 6(a) shows an amplitude of an example object function (left-hand side) and an example probe function (right-hand side). FIG. 6(b) shows a phase of the example object function and probe functions. The brightly-indicated central region of the object indicates an example total area covered by all positions of the illuminating radiation.

Figure 7:
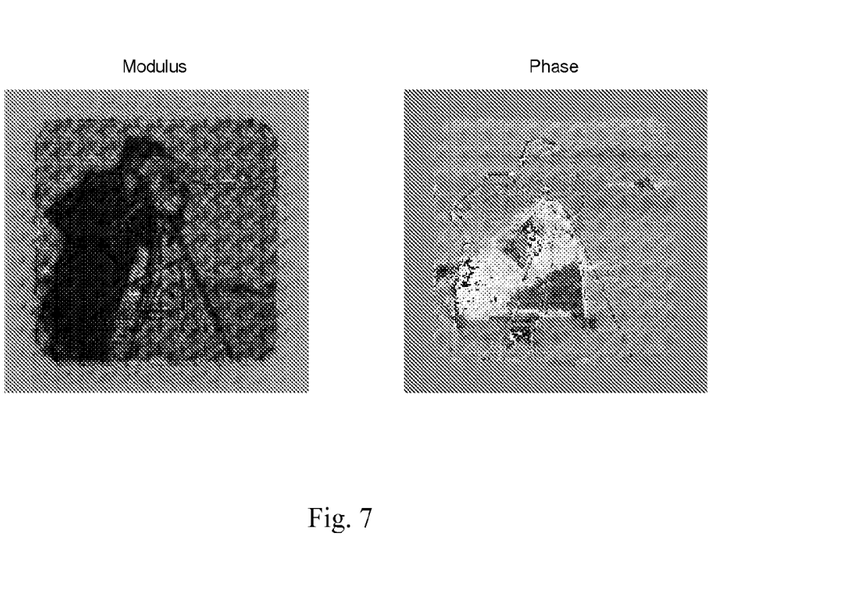
FIG. 7 illustrates an effect of position errors on image data relating to the example object.

FIG. 7 illustrates an estimate of the object function's amplitude (left-hand side) and phase (right-hand side) after 100 iterations when only updating estimates of the object function and probe function i.e. according to an ePIE method as disclosed in WO 2010/064051. It can be appreciated that errors exist in the object function estimate, particularly between individual locations of object function i.e. translation shifts of the object function.

Figure 8:
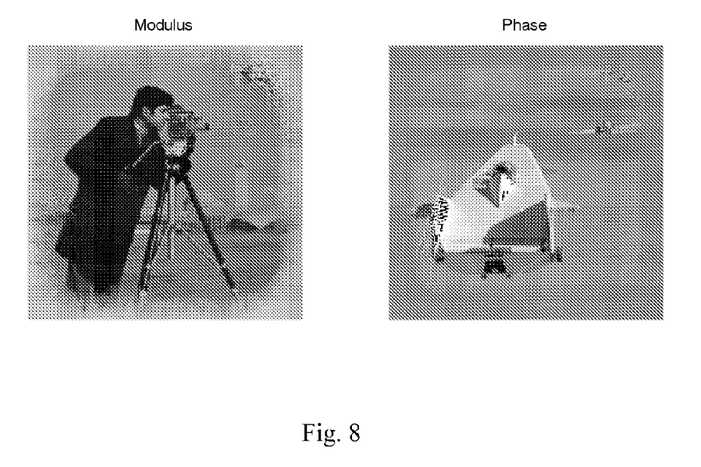
FIG. 8 illustrates the effect of embodiments of the present invention.

FIG. 8 illustrates an estimate of the object function's amplitude (left-hand side) and phase (right-hand side) after 100 iterations when updating estimates of the probe function, as in FIG. 7, and also the translation shift positions according to an embodiment of the invention for the same number of iterations as in FIG. 7. It can be appreciated that the accuracy of the estimate of the image data (object function) is greatly improved i.e. the object function is more accurate or contains less errors for the same number of iterations.

Figure 9:
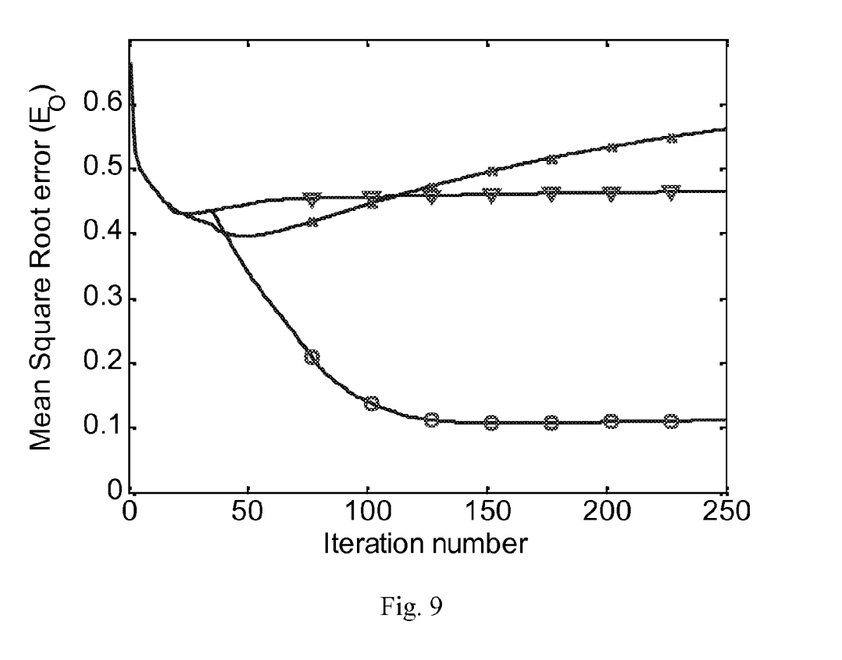
FIG. 9 is a plot of error data showing the effect of embodiments of the present invention.

FIG. 9 illustrates a mean square root error of the object function estimate ($E_O$) after various numbers of iterations of methods according to an embodiment of the invention as shown in FIG. 2. In the example of FIG. 9 the probe function estimate is updated after 35 iterations and the translation shift estimate is updated after 10 iterations, although it will be realised that other numbers of iterations may be used. The line indicated with crosses indicates an error associated with the object function estimate when only updating the probe function estimate from which it can be appreciated that the object function estimate deteriorates over the number of iterations shown. The line indicated with triangles indicates an error associated with the object function estimate when only updating the translation shift estimates, wherein it can be appreciated that the error is slowly reduced over the number of iterations shown. The line indicated with circles indicates an error associated with the object function estimate when updating both the probe function estimate and translation shift estimates, wherein it can be appreciated that the error is significantly reduced.

As noted above with reference to Equation 8 the parameter β controls a strength of feedback of the translation deviation $e_{j,m}$ to updated translation shift estimate $sj_{j;m+1}$. In some embodiments the value of the feedback parameter β is dynamically controlled. The dynamic control of the feeback parameter may cause one or more of: an increase in convergence speed a reduction in error associated with the translation shift estimates and/or prevent instability in the translation shift estimates.

Figure 10:
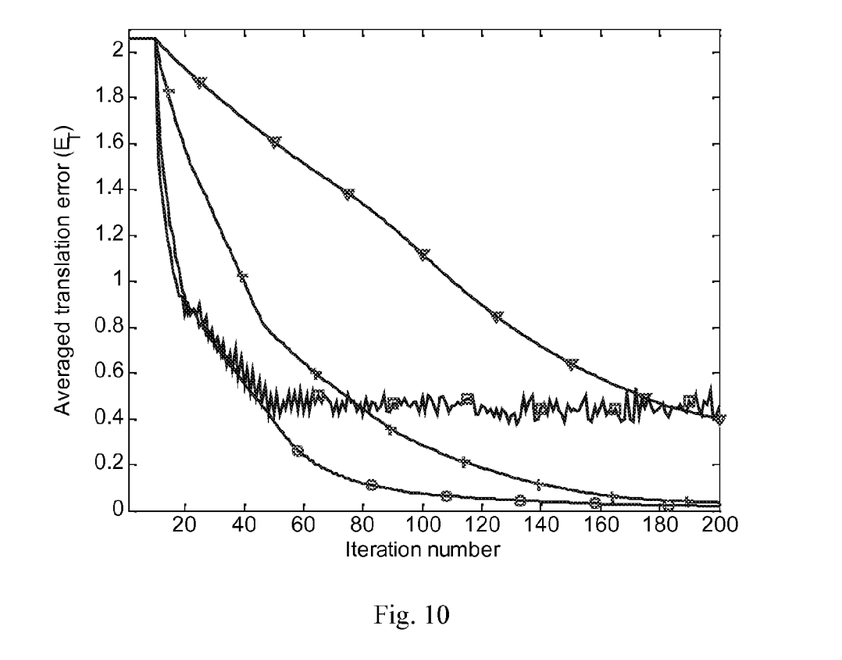
FIG. 10 is a plot of position error data showing the effect of embodiments of the present invention.

FIG. 10 illustrates an average translation error associated with a translation shift position calculated as in Equation 13:

$$E_T = \frac{\sum_j |s_j - s_j^c|}{J}$$

Equation 13 where $s_j^c$ is the correct translation shift value at $j^{th}$ object position. FIG. 10 illustrates the average translation shift position error $E_T$ for different values of β. The line indicated with triangular markers is for β=5; the line with + markers is for β=25 and the line with square markers is for β=120. As can be appreciated, a speed of reduction of the average translation shift position error increases with β. However, beyond a certain limit the final size of the average translation shift position error does not reduce as can appreciated that β=25 eventually leads to less average translation shift position error than β=125. In particular a large value such as β=125 leads to the average translation shift position error including a degree of instability.

Embodiments of the present invention may include dynamic adjustment of the feedback parameter β in order improve a speed of determining the translation shift position, whilst reducing the instability which may be associated with large values of the feedback parameter. Embodiments of the present invention may initially use a relatively large value feedback parameter, such as β=125, although other values may be used. Embodiments of the invention determine an error associated with $e_{j,m}$ Upon detecting an oscillation or instability in $e_{j,m}$, the feedback parameter β may be reduced to avoid the instability. In this way, fast translation shift position error reduction is achieved alongside an overall reduction in the absolute value of the translation shift error.

Figure 11:
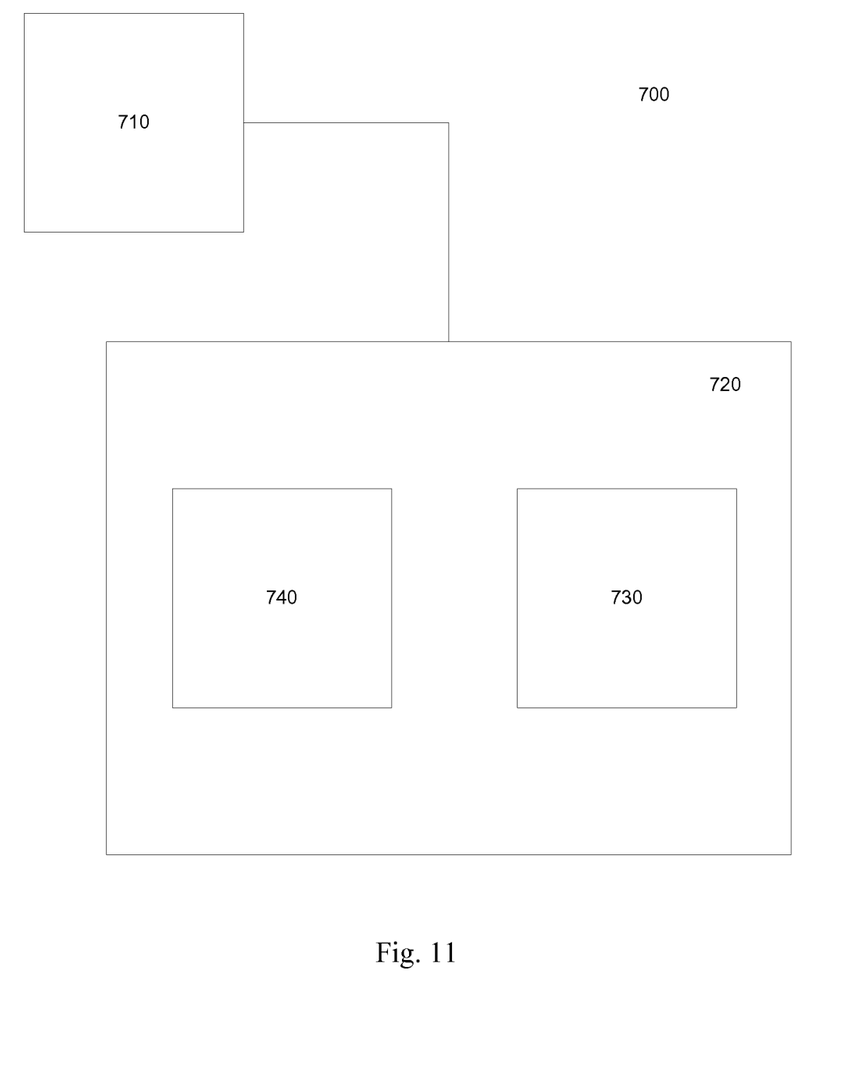
FIG. 11 illustrates an apparatus according to an embodiment of the invention.

FIG. 11 illustrates an apparatus 700 according to an embodiment of the invention. The apparatus 700 is arranged to determine one or more position(s) of an object with respect to incident radiation. The apparatus 700 may also determine one or both of image data or radiation data such as O(r) and/or P(r). The image data may, in some embodiments, be used to generate a visible image of the object. The visible image may, for example, be output to a display device.

The apparatus 700 comprises a detector 710 for detecting an intensity of radiation falling thereon. The detector 710 corresponds to the detector 40 shown in FIG. 1 arranged to record a diffraction pattern formed by radiation scattered by the target object 30. The detector 710 may comprise a plurality of detecting elements each capable of outputting a signal indicative of the intensity of radiation falling thereon. The detector 710 may be a CCD device, or similar. The detector 710 is communicably coupled to a processing unit 720 which is arranged to determine the position of the object 30 with respect to the incident radiation based on the radiation intensity detected by the detector 710. The processing unit 720 comprises a memory 730 and a data processor 740, such as a CPU. Although FIG. 11 shows the processing unit 720 comprising one memory, the processing unit 720 may comprise two or more memories. Furthermore, although shown as comprising one data processor, the processing unit 720 may comprise more than one data processor 740, and each data processor may comprise one or more processing cores. The memory 730 may be arranged to store measured radiation intensity data corresponding to one or a plurality of translation positions. The data processor 740 may implement a method according to an embodiment of the invention, such as that shown in FIG. 2 and/or FIG. 4 as previously described. The data processor may store determined position data in the memory 730.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of determining a position of an object with respect to incident radiation, comprising:
    determining, at a detector, an intensity of radiation scattered by an object;
    iteratively determining, by a processing device, at least one of an object function indicating one or more characteristics of the object and a probe function indicative of one or more characteristics of radiation incident on the object;
    iteratively determining, by the processing device, the position of the object, wherein the iteratively determining the position of the object comprises:
        cross correlating, by the processing device, first and second estimates of the object function or the probe function;
        determining, by the processing device, a location of a peak of the cross correlation;
    determining, by the processing device, a translation deviation indicative of an improvement in determination of the position of the object with respect to the radiation incident on the object between the first and second estimates based on the location of the peak;
    wherein the iteratively determining, by the processing device, at least one of the object function and the probe function comprises determining, by the processing device, a third estimate of the object function or the probe function based on the translation deviation; and
    outputting one or more of the object function, probe function and an indication of the position of the object.

2. The method of claim 1, wherein the position of the object with respect to the incident radiation is determined at least in part on the translation deviation.

3. The method of claim 2, wherein the position of the object with respect to the incident radiation is based on the translation deviation and a feedback value.

4. The method of claim 3, wherein the feedback value is dynamically adjusted.

5. The method of claim 4, wherein the dynamic adjustment is based on the translation deviation.

6. The method of claim 4, wherein the dynamic adjustment is provided to reduce the feedback value to avoid instability.

7. The method of claim 1, wherein the first estimate is a prior estimate of the object function or the probe function and the second estimate is an updated estimate of the object function or the probe function, the method further comprising:
    transposing and conjugating the first estimate and determining a transform thereof and determining a transform of the second estimate.

8. The method of claim 7, further comprising:
    multiplying the transforms of the transposed and conjugated first estimate and the second estimate.

9. The method of claim 8, further comprising:
    inversely transforming the multiplied transforms of the transposed and conjugated first estimate and the second estimate.

10. The method of claim 9, wherein the location of the peak of the cross correlation is determined based on the inversely transformed first estimate and the second estimate.

11. The method of claim 1, wherein the determining the location of the peak of the cross correlation comprises:
    determining an integer location of the peak and a sub-integer location of the peak.

12. The method of claim 11, further comprising:
    transposing and conjugating the first estimate and determining a transform thereof and determining a transform of the second estimate;
    multiplying the transforms of the transposed and conjugated first estimate and the second estimate; and
    zero padding the multiplied transforms to determine the sub-integer location of the peak.

13. The method of claim 11, further comprising:
    transposing and conjugating the first estimate and determining a transform thereof and determining a transform of the second estimate;
    multiplying the transforms of the transposed and conjugated first estimate and the second estimate; and
    determining an approximate location of the peak and only multiplying a region of the transforms corresponding to the approximate location of the peak to determine the sub-integer location of the peak.

14. The method of claim 1, wherein the position of the object with respect to the incident radiation is determined for a plurality of positions.

15. The method of claim 12, wherein the plurality of positions are positions of the object with respect to the incident radiation.

16. The method of claim 13, wherein in a first iteration of the method an initial estimate of one or both the object function and/or the probe function is utilised.

17. The method of claim 1, further comprising:
    updating only one of the object function and the probe function for a first plurality of iterations.

18. The method of claim 17, wherein the position of the object with respect to the incident radiation is determined following a second plurality of iterations.

19. The method of claim 1, wherein the position of the object is determined based upon the translation deviation and a currently estimated position of the object.

20. The method of claim 1, wherein the cross correlation of the first and second estimates of the object function or the probe function are determined in a frequency domain.

21. The method of claim 1, wherein the position of the object with respect to the incident radiation is determined iteratively alongside an estimate of one or both the object function or the probe function for at least some iterations.

22. An apparatus for determining a position of an object with respect to incident radiation, comprising:
a detector for measuring an intensity of a wavefield incident thereon scattered from an object; and
a processing device arranged:
to receive intensity data from the detector,
to iteratively determine at least one of an object function indicating one or more characteristics of the object and a probe function indicative of one or more characteristics of incident radiation, and
to iteratively determine the position of the object with respect to the incident radiation by:
cross correlating first and second estimates of the object function or the probe function indicating of one or more characteristics of the incident radiation,
determining a location of a peak of the cross correlation, and
determining a translation deviation indicative of an improvement in determination of the position of the object with respect to the radiation incident on the object between the first and second estimates based on the location of the peak;
wherein the iteratively determining at least one of the object function and the probe function comprises determining a third estimate of the object function or the probe function based on the translation deviation.

23. The apparatus of claim 22, wherein the first estimate is a prior estimate of the object function or the probe function and the second estimate is an updated estimate of the object function or the probe function, wherein the processing device is further arranged to:
transpose and conjugate the first estimate and to determine a transform thereof and determine a transform of the second estimate.

24. The apparatus of claim 23, wherein the processing device is further arranged to:
multiply the transforms of the transposed and conjugated first estimate and the second estimate.

25. The apparatus of claim 24, wherein the processing device is further arranged to:
inversely transform the multiplied transforms of the transposed and conjugated first estimate and the second estimate.

26. The apparatus of claim 25, wherein the processing device is further arranged to:
determine the location of the peak of the cross correlation based on the inversely transforming the multiplied transforms of the transposed and conjugated first estimate and the second estimate.

27. The apparatus of claim 22, wherein the processing device is further arranged to:
determine the location of the peak of the cross correlation by determining an integer location of the peak and a sub-integer location of the peak.

28. The apparatus of claim 27, wherein the processing device is further arranged to:
transpose and conjugate the first estimate and to determine a transform thereof and determine a transform of the second estimate;
multiply the transforms of the transposed and conjugated first estimate and the second estimate; and
zero pad the multiplied transforms to determine the sub-integer location of the peak.

29. The apparatus of claim 27, wherein the processing device is further arranged to:
transpose and conjugate the first estimate and to determine a transform thereof and determine a transform of the second estimate;
multiply the transforms of the transposed and conjugated first estimate and the second estimate; and
determine an approximate location of the peak and to only multiply a region of the transforms corresponding to the approximate location to determine the sub-integer location of the peak.

30. The apparatus of claim 22, wherein the position of the object with respect to the incident radiation is based on the translation deviation and a current estimate of the location of the object.

31. The apparatus of claim 22, wherein the processing device is further arranged to:
determine the position of the object with respect to the incident radiation based on the translation deviation and a feedback value.

32. The apparatus of claim 22, wherein the processing device is further arranged to:
determine the cross correlation of the first and second estimates of the object function or the probe function in a frequency domain.

33. A non-transitory computer-readable medium containing computer executable instructions which, when executed by a computer, perform operations comprising:
determining, at a detector, an intensity of radiation scattered by an object;
iteratively determining, by a processing device, at least one of an object function indicating one or more characteristics of the an object and a probe function indicative of one or more characteristics of incident radiation incident on the object;
iteratively determining, by the processing device, a position of the object, wherein the iteratively determining the position of the object comprises:
cross correlating, by the processing device, first and second estimates of the object function or the probe function;
determining, by the processing device, a location of a peak of the cross correlation;
determining, by the processing device, a translation deviation indicative of an improvement in determination of the a difference in position of the object with respect to the radiation incident on the object between the first and second estimates based on the location of the peak;
wherein the iteratively determining, by the processing device, at least one of the object function and the probe function comprises determining, by the processing device, a third estimate of the object function or the probe function based on the translation deviation; and
outputting one or more of the object function, probe function and an indication of the position of the object.

* * * * *